(12) United States Patent
Bertrand et al.

(10) Patent No.: US 10,101,179 B2
(45) Date of Patent: Oct. 16, 2018

(54) ELECTROMAGNETIC POSITION TRACKING SYSTEM

(71) Applicants: Commissariat à l'Energie Atomique et aux Energies Alternatives, Paris (FR); MinMaxMedical, La Tronche (FR)

(72) Inventors: François Bertrand, Seyssins (FR); Vincent Josselin, Grenoble (FR); Loïc Huguel, La Tronche (FR); Sandra Rousseau, La Tronche (FR)

(73) Assignees: COMMISSARIAT À L'ENERGIE ATOMIQUE ET AUX ENERGIES ALTERNATIVES, Paris (FR); MINMAXMEDICAL, La Tronche (FR)

( * ) Notice: Subject to any disclaimer, the term of this patent is extended or adjusted under 35 U.S.C. 154(b) by 125 days.

(21) Appl. No.: 15/215,440

(22) Filed: Jul. 20, 2016

(65) Prior Publication Data

US 2017/0023381 A1    Jan. 26, 2017

(30) Foreign Application Priority Data

Jul. 20, 2015  (FR) ...................................... 1556827

(51) Int. Cl.
*G01D 5/20*    (2006.01)
*A61B 34/20*   (2016.01)
*A61B 90/00*   (2016.01)

(52) U.S. Cl.
CPC ........... *G01D 5/2006* (2013.01); *A61B 34/20* (2016.02); *A61B 90/39* (2016.02); *G01D 5/204* (2013.01); *A61B 2034/2051* (2016.02); *A61B 2034/2072* (2016.02); *A61B 2090/397* (2016.02); *A61B 2090/3983* (2016.02)

(58) Field of Classification Search
CPC .................................................... G01D 5/2053
USPC .................................................... 324/207.17
See application file for complete search history.

(56) References Cited

U.S. PATENT DOCUMENTS

| | | |
|---|---|---|
| 6,172,499 B1 | 1/2001 | Ashe |
| 7,321,228 B2 | 1/2008 | Govari |
| 7,373,271 B1 | 5/2008 | Schneider |
| 2003/0184285 A1 | 10/2003 | Anderson et al. |
| 2004/0207389 A1 | 10/2004 | Nieminen et al. |
| 2005/0165297 A1 | 7/2005 | Anderson et al. |

(Continued)

FOREIGN PATENT DOCUMENTS

WO    2003102497 A1    12/2003

OTHER PUBLICATIONS

Preliminary Search Report in French Patent Application No. 1556827, dated May 11, 2016, 2 pages.

*Primary Examiner* — Jermele M Hollington
*Assistant Examiner* — Douglas X Rodriguez
(74) *Attorney, Agent, or Firm* — Moreno IP Law LLC

(57) ABSTRACT

The invention relates to an electromagnetic position tracking system, including: an electromagnetic field emission device including at least one emitter coil and, connected to the emitter coil, a first generator of an electric signal for exciting the emitter coil; a device for receiving the electromagnetic field emitted by the emission device, including at least one receiver coil, and, connected to the receiver coil, a circuit for reading an electric signal induced in the receiver coil; and a system for measuring at least one parameter of the reception device, including, connected to the receiver coil, a second generator of an electric signal for exciting the receiver coil.

11 Claims, 2 Drawing Sheets

(56) References Cited

U.S. PATENT DOCUMENTS

2005/0246122 A1 11/2005 Jones, Jr. et al.
2013/0296651 A1 11/2013 Ito et al.
2014/0002063 A1 1/2014 Ashe

ELECTROMAGNETIC POSITION TRACKING SYSTEM

CROSS-REFERENCE TO RELATED APPLICATION

The instant application claims the benefit of French patent application number 15/56827, filed Jul. 20, 2015, the teachings of which are incorporated herein by this reference.

BACKGROUND

The present application relates to electromagnetic position tracking systems or electromagnetic locating systems. It more specifically aims at electromagnetic position tracking systems adapted to the medical field, for example, to locate one or a plurality of tools used by a surgeon during a medical operation.

DISCUSSION OF THE RELATED ART

Position tracking systems of the type comprising the following elements are here more particularly considered:
an electromagnetic field emission device comprising one of a plurality of emitter coils; and
a device for receiving this field comprising one or a plurality of receiver coils.

In such a system, the conjoint analysis of the fields emitted by the emitter coils and of the fields received by the receiver coils enables to determine the position and/or the orientation of the receiver device with respect to the emission device.

An example of such a system is for example described in patent application US2005/0165297.

An electromagnetic position tracking system having an improved performance over known systems, particularly in terms of location accuracy, is needed.

SUMMARY

Thus, an embodiment provides an electromagnetic position tracking system comprising: an electromagnetic field emission device comprising at least one emitter coil and, connected to the emitter coil, a first generator of an electric signal for exciting the emitter coil; a device for receiving the electromagnetic field emitted by the emission device, comprising at least one receiver coil, and, connected to the receiver coil, a circuit for reading an electric signal induced in the receiver coil; and a system for measuring at least one parameter of the reception device, comprising, connected to the receiver coil, a second generator of an electric signal for exciting the receiver coil.

According to an embodiment, the parameter is a parameter from the group comprising the series resistance and the self-inductance of the receiver coil.

According to an embodiment, the reception device comprises at least two receiver coils, and the parameter is a parameter from the group comprising the series resistance of each receiver coil, the self-inductance of each receiver coil, and the coefficient of mutual inductance between two receiver coils.

According to an embodiment, the parameter comprises the series resistance of each receiver coil, and the measurement system is capable, to measure the series resistance, of applying to one end of the receiver coil a DC voltage or a sinusoidal voltage having a frequency at least 20 times lower than the cut-off frequency of the coil.

According to an embodiment, the parameter comprises the self-inductance of each receiver coil, and the measurement system is capable, to measure the self-inductance, of applying on one end of the receiver coil a sinusoidal voltage having a frequency greater than the cut-off frequency of the coil.

According to an embodiment, the parameter comprises the coefficient of mutual inductance between the two receiver coils, and the measurement system is capable, to measure the coefficient, of applying on one end of one of the two receiver coils a sinusoidal voltage having a frequency greater than the cut-off frequency of the coil.

According to an embodiment, the read circuit comprises, associated with each receiver coil, a sense amplification stage comprising an operational amplifier having its inverting input coupled to the output via a feedback resistor and having its non-inverting input coupled to a node of application of a reference potential, a first end of the receiver coil being connected to the inverting input of the operational amplifier.

According to an embodiment, the second generator comprises, associated with each receiver coil, a controllable voltage source connected between the second end of the receiver coil and the node of application of a reference potential.

According to an embodiment, the second generator comprises a digital frequency synthesizer.

According to an embodiment, the emitter coil comprises three emitter coils oriented along different axes, and the receiver coil comprises three receiver coils oriented along different axes.

The foregoing and other features and advantages will be discussed in detail in the following non-limiting description of specific embodiments in connection with the accompanying drawings.

DETAILED DESCRIPTION

Figure 1:
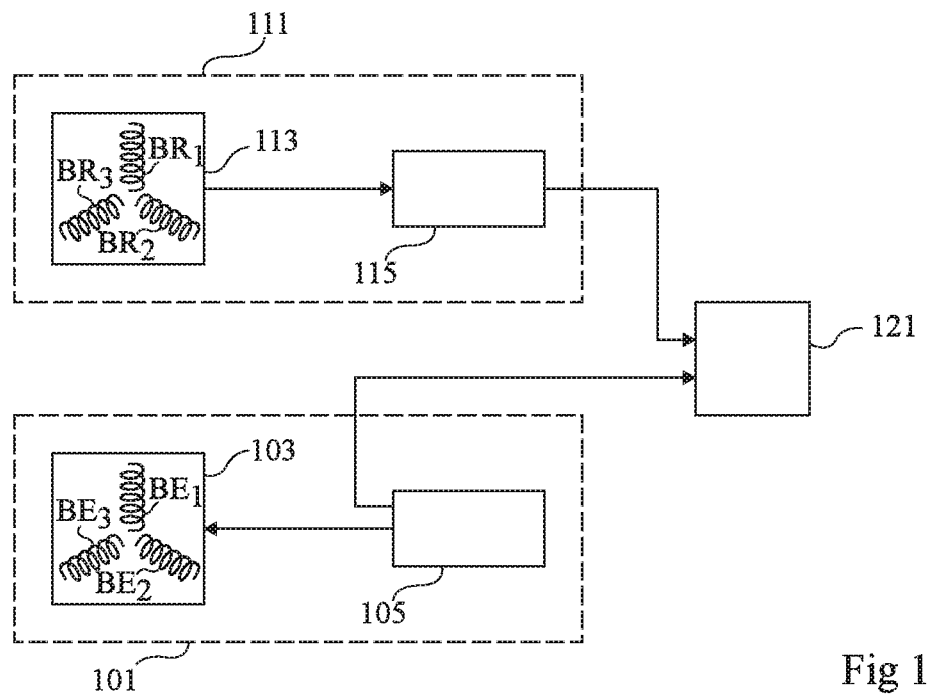
FIG. 1 schematically shows in the form of blocks an example of an electromagnetic position tracking system.

The same elements have been designated with the same reference numerals in the different drawings. For clarity, only those elements which are useful to the understanding of the described embodiments have been shown and are detailed. In particular, the calculation algorithms enabling, based on the values of the fields emitted by the emitter coils and received by the receiver coils, to determine the position and/or the orientation of the reception device with respect to the emission device, are not detailed. Indeed, the described embodiments are compatible with usual algorithms for determining the position and/or orientation information of the reception device based on the measured field values. Unless otherwise specified, expressions "substantially" and "in the order of" mean to within 10%, preferably to within 5%. Further, in the present description, term "connected" will be used to designate a direct electric connection, with no intermediate electronic component, for example, by means of one or a plurality of conductive tracks or conductive wires, and term "coupled" or term "linked" is used to designate either a direct electric connection (then meaning "connected") or a connection via one or a plurality of intermediate components (resistor, capacitor, etc.).

FIG. 1 schematically shows in the form of blocks an example of an electromagnetic position tracking system.

The system of FIG. 1 comprises an electromagnetic field emission device 101 comprising an assembly 103 of one or a plurality of emitter coils. The case of a system where assembly 103 comprises three emitter coils $BE_1$, $BE_2$ and $BE_3$ oriented along three different axes, for example, along the three axes of an orthogonal reference frame, is here considered. Emission device 101 further comprises a device 105 for generating AC electric signals (voltage or currents) for exciting the coils of assembly 103, for example, sinusoidal signals. Generator 105 is connected to at least one terminal of each of coils $BE_1$, $BE_2$ and $BE_3$.

The system of FIG. 1 further comprises a device 111 for receiving the electromagnetic field emitted by emission device 101. Reception device 111 comprises an assembly 113 of one or a plurality of receiver coils. The case of a system where assembly 113 comprises three receiver coils $BR_1$, $BR_2$ and $BR_3$ oriented along three different axes, for example, along the three axes of an orthogonal reference frame, is here considered as an example. Reception device 111 further comprises a device 115 for reading the electric signals (voltages or currents) induced in the coils of assembly 113 under the effect of the AC fields emitted by the emitter coils.

The system of FIG. 1 further comprises a processing device 121, for example comprising a microprocessor, coupled on the one hand to generator 105 of emission device 101 and on the other hand to read device 115 of reception device 111. The connections between generator 105 and processing device 121 and between read device 115 and processing device 121 may be wire connections or wireless connections. Generator 105 is capable of transmitting to processing device 121 signals representative of the excitation signals that it applies to the terminals of emitter coils $BE_1$, $BE_2$ and $BE_3$. Read device 115 is capable of transmitting to processing device 121 signals representative of the signals read across receiver coils $BR_1$, $BR_2$ and $BR_3$. The signals transmitted by devices 105 and 115 to processing device 121 are for example digital signals. As an example, generator 105 comprises a circuit (not shown) for sampling and digitizing the analog excitation signals applied across emitter coils $BE_1$, $BE_2$ and $BE_3$, and read device 115 comprises a circuit (not shown) for sampling and digitizing the analog signals read across receiver coils $BR_1$, $BR_2$ and $BR_3$.

The locating system of FIG. 1 operates as follows.

Assembly 103 of emitter coils of emission device 101 defines a reference frame for the location of assembly 113 of receiver coils of reception device 111. Assembly 113 of receiver coils may be secured to an object to be located. As an example, in the case of an application to the locating of a surgical tool, assembly 103 of emitter coils may be secured to a patient's body or on a structure external to the patient's body used as a reference frame. The assembly 113 of receiver coils may be secured to a surgical tool which is desired to be located during the operation.

During a phase of tracking the position of the object to be located, emitter coils $BE_1$, $BE_2$ and $BE_3$ of emission device 101, controlled by generator 105, each emit an AC electromagnetic field. As an example, generator 105 is configured to simultaneously apply excitation signals of different frequencies to the different coils of assembly 103, in which case the coils of assembly 103 simultaneously emit AC electromagnetic fields having different frequencies. This enables, at the level of the reception device, to be able to spectrally discriminate the fields originating from the different emitter coils. As a variation, the generator is configured to sequentially apply to the different coils of assembly 103 excitation signals of same frequency, so that at a given time, only one of the coils of assembly 103 emits an electromagnetic field. This enables, at the level of the reception device, to be able to discriminate in time the fields originating from the different emitter coils. The emission frequency or frequencies of device 101 are for example in the range from 1 to 50 kHz. Signals (for example digital) representative of the excitation signals applied by generator 105 to coils $BE_1$, $BE_2$ and $BE_3$, are transmitted to processing unit 121.

At the level of reception device 111, the electric signals are induced in receiver coils $BR_1$, BR2 and $BR_3$ under the effect of the electromagnetic fields emitted by emitter coils $BE_1$, $BE_2$ and $BE_3$. These signals are measured by read device 115 and transmitted (for example, in digital form) to processing unit 121.

Processing device 121 comprises a synchronous demodulation and filtering unit (not shown in the drawing) capable, based on signals transmitted by generator 105 and read device 115, of determining, for each of the receiver coils of assembly 113, the intensity of the field captured by the coil from each of the emitter coils of assembly 103. Based on the intensity of the fields captured by the receiver coils, processing device 121 determines the position and/or the orientation of the assembly of receiver coils 113 with respect to the assembly of emitter coils 103. More particularly, in the example of FIG. 1, the synchronous demodulation and filtering unit determines nine field values respectively corresponding to the field received by coil $BR_1$ from coil $BE_1$, to the field received by coil $BR_1$ from coil $BE_2$, to the field received by coil $BR_1$ from coil $BE_3$, to the field received by coil $BR_2$ from coil $BE_1$, to the field received by coil $BR_2$ from coil $BE_2$, to the field received by coil $BR_2$ from coil $BE_3$, to the field received by coil $BR_3$ from coil $BE_1$, to the field received by coil $BR_3$ from coil $BE_2$, and to the field received by coil $BR_3$ from coil $BE_3$. Based on these nine field values, processing unit 121 calculates the spatial position coordinates of all the receiver coils 113 along three axes of the reference frame defined by the emitter coils, and three angular values defining the orientation of all the receiver coils 113 with respect to the axes of the reference frame defined by the emitter coils (it is spoken of a locating system with six degrees of freedom).

The accuracy of a locating system of the type described in relation with FIG. 1 particularly depends on the accuracy of the measurement of the fields captured by the coils of the reception device. Thus, to obtain a good locating accuracy, the transfer function of conversion of the field values of the electric signals (voltages or currents) measured across the coils of reception device 111 should be accurately known.

The case where read device 115 of reception device 111 comprises a transimpedance-type amplification device is here more particularly considered. An example of such an amplification device is illustrated in FIG. 2.

Figure 2:
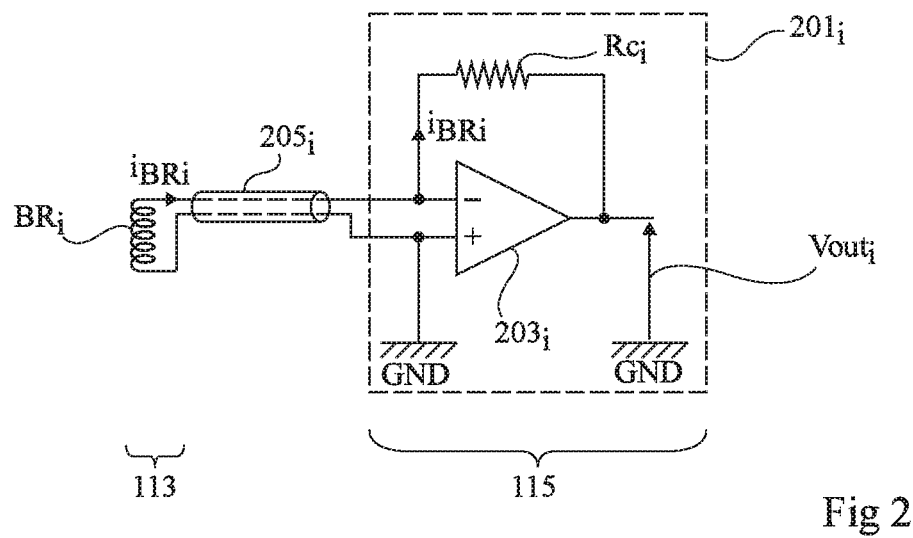
FIG. 2 shows in further detail a portion of the reception device of the electromagnetic position tracking system of FIG. 1.

FIG. 2 shows in further detail a portion of reception device 111 of an electromagnetic system position tracking system of the type described in relation with FIG. 1.

In the example of FIG. 2, read device 115 comprises, associated with each of receiver coils $BR_i$, with i being an integer from 1 to 3, an amplification device $201_i$ of transimpedance type, that is, comprising an operational amplifier $203_i$ having its inverting input (−) coupled to its output by a feedback resistor $Rc_i$ and having its non-inverting input (+) coupled to a node of application of a reference potential GND, for example, the ground. For simplification, only one coil $BR_i$ and one amplification device $201_i$ associated with this coil have been shown in FIG. 2.

Coil $BR_i$ has its two ends connected, for example, via a coaxial cable $205_i$, respectively to the inverting input (−) and to the non-inverting input (+) of operational amplifier $203_i$.

In such an assembly, coil $BR_i$ is shorted due to the virtual ground present on the inverting input (−) of operational amplifier $203_i$. Coil $BR_i$ conducts a current $i_{BRi}$ proportional to the intensity of the magnetic field received by the coil.

In operation, operational amplifier $203_i$ delivers on its output node a voltage $Vout_i$ (referenced with respect to node GND) which is an amplified image of current $i_{BRi}$.

Read device 115 may further comprise, associated with each of receiver coils $BR_i$, a sampling and digitization circuit (not shown) capable of sampling and digitizing voltage $Vout_i$, the digital output of this circuit being coupled to processing device 121.

The transfer function or magnetic field/voltage conversion gain of such an assembly may be expressed as follows:

$$K_{BRi}(j\omega) = \frac{V_{outi}}{B} = -\frac{M_{BRi}}{L_{BRi}} Rc_i \frac{\frac{L_{BRi}}{Rs_{BRi}} j\omega}{1 + \frac{L_{BRi}}{Rs_{BRi}} j\omega}$$

where B designates the intensity of the magnetic field received by coil $BR_i$, j designates the imaginary unit, ω designates the pulse of field B (ω=2πf, f being the frequency of field B), $M_{BRi}$ designates the magnetic moment per current unit of coil $BR_i$, in A·m²/A, $L_{BRi}$ designates the inductance of coil $BR_i$, $Rs_{BRi}$ designates the series resistance of the circuit connected between the inverting input (−) and the non-inverting input (+) of operational amplifier $203_i$, particularly comprising, in this example, the resistance of coil $BR_i$ and the resistance of cable $205_i$, and $K_{BRi}(j\omega)$ designates the field/voltage proportionality coefficient at pulse ω.

The frequency response of conversion gain $K_{BRi}$ is a response of high-pass type, with a gain equal to $(M_{BRi}/L_{BRi})*Rc_i$, and a cut-off frequency equal to $Rs_{BRi}/(2\pi L_{BRi})$.

To accurately know the magnetic field/voltage transfer function of such an assembly, one needs to accurately know parameters $L_{BRi}$ and $Rs_{BRi}$ of the assembly.

The accurate knowledge of the value of resistor $Rs_{BRi}$ raises a specific issue since this value is likely to vary by relatively large proportions under the effect of the temperature variations to which receiver coils $BR_i$ may be submitted.

The value of inductance $L_{BRi}$, although it is less dependent on temperature variations, however remains capable of drifting (particularly depending on the materials used, such as for example, the use or not of a ferromagnetic core). It may further be useful to accurately know this value in a phase of calibration of the electromagnetic system to constrain certain coefficients used by the calculation algorithm for determining the position and/or the orientation.

Further, in the case of a reception device with a plurality of coils of the type shown in FIG. 1, a phenomenon of parasitic coupling of receiver coils $BR_i$ with one another occurs. More particularly, each coil emits back a parasitic magnetic field proportional to the induced current that it conducts, this parasitic field being itself captured by the other receiver coils. Thus, for example, in the configuration with three receiver coils of FIG. 1, field B captured by receiver coil $BR_3$ will comprise not only the useful field which is desired to be measured, that is, the field emitted by coils $BE_1$, $BE_2$ and $BE_3$ of emission device 101, but also a parasitic field emitted back by receiver coil $BR_1$, and a parasitic field emitted back by receiver coil $BR_2$. To determine the useful field captured by each of coils $BR_i$, the parasitic fields emitted by the other receiver coils of assembly 113 have to be known. To achieve this, the mutual inductance coefficient between the different receiver coils should be accurately known. In particular, in the case of a transimpedance assembly of the type described in relation with FIG. 2, the parasitic field received by a receiver coil $BR_i$ from another receiver coil $BR_{i'}$ (i' being an integer from 1 to 3 different from i) is equal to $$\frac{Ml_{i,i'}}{M_{BRi}} i_{BRi'} = \frac{Ml_{i,i'}}{M_{BRi}} \frac{V_{outi'}}{Rc_{i'}}$$

where $Ml_{i,i'}$ designates the coefficient of mutual inductance between coils $BR_i$ and $BR_{i'}$.

The values of the mutual inductance coefficients are little dependent on temperature variations, and fluctuate little on the short term. However, in the same way as for inductance values $L_{BRi}$, it may be useful to know the mutual inductance coefficients in the electromagnetic calibration phase to constrain certain coefficients used by the calculation algorithm for determining the position and/or the orientation.

Figure 3:
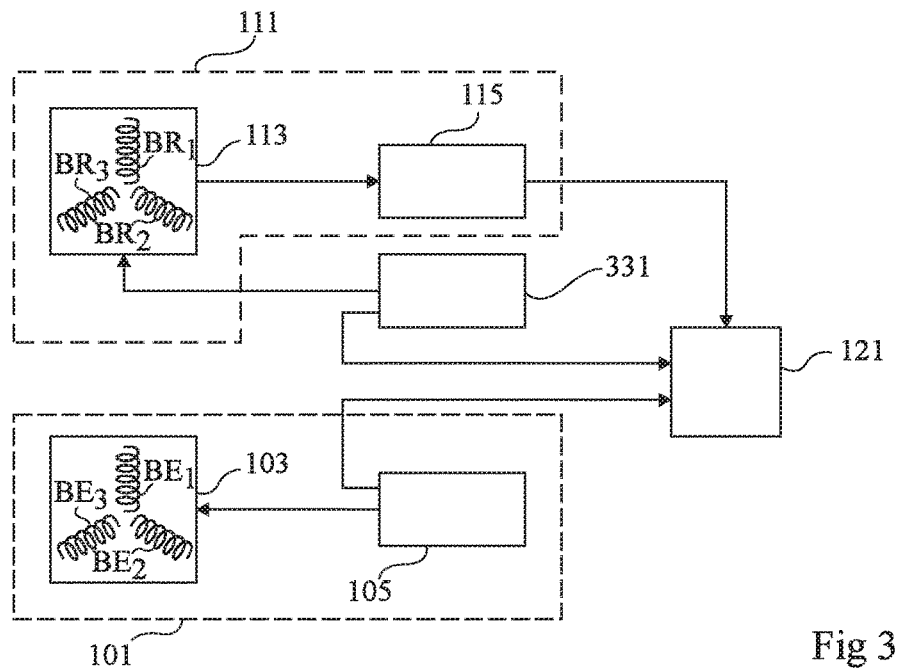
FIG. 3 schematically shows in the form of blocks an embodiment of an electromagnetic position tracking system.

FIG. 3 schematically shows in the form of blocks an embodiment of an electromagnetic position tracking system.

The system of FIG. 3 comprises elements common with the system of FIG. 1. These elements will not be detailed again. In the following description, only the differences between the system of FIG. 3 and the system of FIG. 1 will be detailed.

The system of FIG. 3 differs from the system of FIG. 1 in that it comprises, in addition to emission device 101, reception device 111 and processing unit 121, a system for measuring parameters of reception device 111, the measurement system enabling to determine in situ, that is, during a phase of use of the locating system to follow the position of an object, the values of parameters $Rs_{BRi}$ and/or $L_{BRi}$ and/or $Ml_{i,i'}$ of the assembly formed by receiver coils $BR_i$ and sense amplification stages $201_i$ associated with the receiver coils.

The parameter measurement system comprises a controllable device 331 for generating electric signals (voltages or currents) for exciting the receiver coils of assembly 113. Generator 331 is connected to at least one terminal of each of receiver coils $BR_1$, $BR_2$ and $BR_3$.

Generator 331 is coupled to processing device 121 by a wire or wireless connection. Generator 331 is capable of transmitting to processing device 121 signals (for example, digital) representative of the excitation signals that it applies to the terminals of receiver coils $BR_1$, $BR_2$ and $BR_3$.

Figure 4:
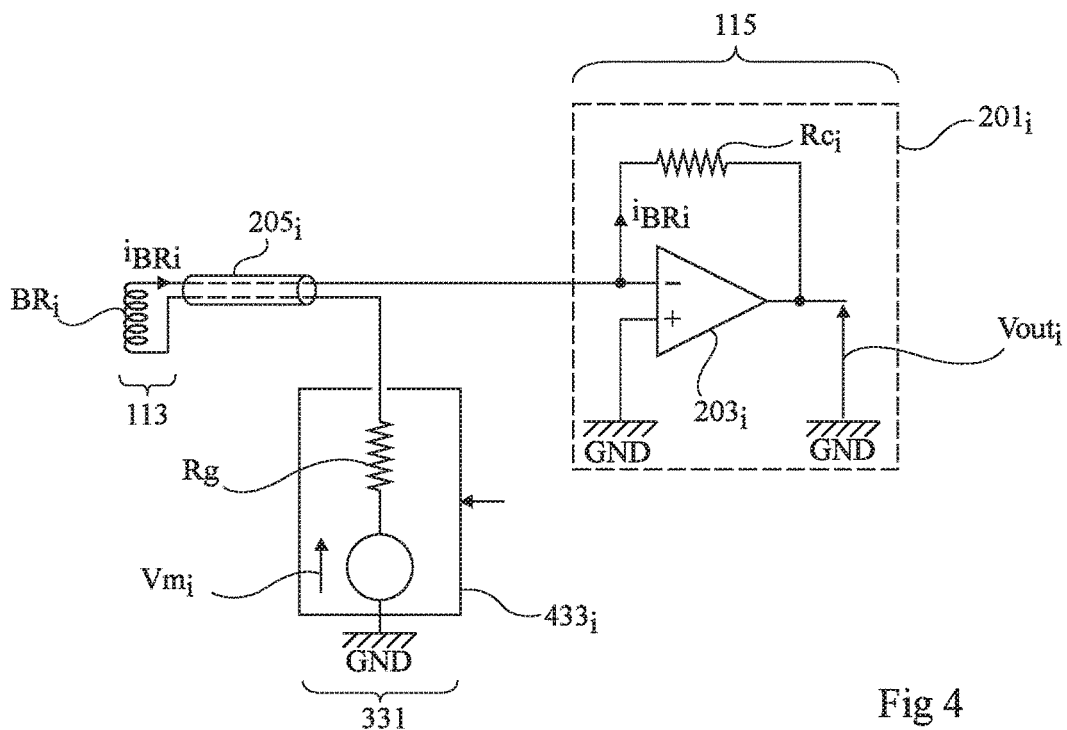
FIG. 4 shows in further detail a portion of the electromagnetic position tracking system of FIG. 3.

FIG. 4 shows in further detail a portion of the locating system of FIG. 3.

In the example of FIG. 4, read device 115 comprises, as in the example of FIG. 2, associated with each of receiver coils $BR_i$, an amplification device $201_i$ of transimpedance type, comprising an operational amplifier $203_i$ having its inverting input (−) coupled to its output by a feedback resistor $Rc_i$ and having its non-inverting input (+) coupled to a node of application of a reference potential GND, for example, the ground.

In the example of FIG. 4, generator 331 comprises, associated with each of receiver coils $BR_i$, a controllable current source $433_i$ connected to an end of coil $BR_i$ and capable of applying a voltage $Vm_i$, referenced with respect to node GND, to this end of coil $BR_i$.

The other end of coil $BR_i$ is connected to the inverting input (−) of operational amplifier $203_i$.

For simplification, only one coil $BR_i$, one amplification device $201_i$ associated with this coil, and one controllable voltage source $433_i$ associated with this coil have been shown in FIG. 4.

As an example, a cable $205_i$, for example, a coaxial cable, couples the two ends of coil $BR_i$ respectively to the inverting input (−) of operational amplifier $203_i$ and to the output of controllable voltage source $433_i$.

In this assembly, coil $BR_i$ is not directly connected to the non-inverting input (+) of operational amplifier $203_i$, but is coupled to the non-inverting input (+) via controllable current source $433_i$ and reference node GND.

The operation of the electromagnetic locating system of FIGS. 3 and 4 is identical or similar to that of FIGS. 1 and 2 in that it concerns actual position tracking operations, with the difference that, in the system of FIGS. 3 and 4, the series resistance $Rs_{BRi}$ associated with receiver coil $BR_i$, that is, the series resistance of the circuit connected between the inverting input (−) and the non-inverting input (+) of operational amplifier $203_i$, comprises not only the resistance of coil $BR_i$ and the resistance of cable $205_i$, but further comprises series resistance $R_g$ of controllable current source $433_i$.

The operation of the system for measuring parameters of reception device 101 of the electromagnetic locating system of FIGS. 3 and 4 will now be described in the next three cases: A) to measure the series resistance $Rs_{BRi}$ associated with a receiver coil $BR_i$, B) to measure the inductance $L_{BRi}$ of a receiver coil $BR_i$, and C) to measure the coefficient $Ml_{i,i'}$ of mutual inductance between two receiver coils $BR_i$ and $BR_{i'}$.

A) measurement of series resistance $Rs_{BRi}$

To measure the series resistance $Rs_{BRi}$ associated with a coil $BR_i$, generator 331 controls the application, via controllable voltage source $433_i$, of a DC or sinusoidal voltage $Vm_i$ on the terminal of coil $BR_i$ connected to voltage source $433_i$.

In the case of a sinusoidal voltage $Vm_i$, the latter may be expressed as follows:

$$Vm_i(t) = V_{ref}\cos(2\pi f_i t)$$

where $V_{ref}$ designates the amplitude of the sinusoidal voltage and $f_i$ designates the frequency thereof.

Voltage $Vm_i$ is amplified by transimpedance amplification stage $201_i$, the amplified image of this voltage forming a component of output voltage $V_{outi}$ of amplification stage $201_i$. Frequency $f_i$ of voltage $Vm_i$ is preferably selected to be much smaller than the cut-off frequency of the coil (equal to $Rs_{BRi}/2\pi L_{BRi}$), so that the impedance of the inductance of coil $BR_i$ can be neglected as compared with the series resistance to be measured. As an example, frequency $f_i$ is selected to be at least 20 times smaller than the cut-off frequency of the coil. As an example, frequency $f_i$ may be in the range from 1 to 20 Hz for a cut-off frequency of the coil substantially equal to 1 kHz. Amplitude $V_{ref}$ of the sinusoidal voltage is selected to avoid saturating operational amplifier $203_i$, that is, so that output voltage $V_{outi}$ of the amplification stage remains lower than the saturation output voltage of amplifier $203_i$.

Processing device 121 comprises a synchronous detection unit (not shown in the drawing) capable of extracting peak value $V_{outifi}$ of the frequency component $f_i$ of signal $V_{outi}$. Based on peak value $V_{outifi}$, processing device 121 may determine the value of series resistance $Rs_{BRi}$ by the following formula:

$$Rs_{BRi} = \frac{Rc_i}{2}\frac{V_{ref}}{V_{outifi}}$$

In the case of a DC voltage $Vm_i$ of value $V_{ref}$, only the processing implemented by the detection unit differs from what has just been described. This processing may be a simple low-pass filtering enabling to directly extract DC component $V_{outic}$ from voltage $V_{outi}$. Processing device 121 can then determine the values of series resistance $Rs_{BRi}$ by the following formula:

$$Rs_{BRi} = Rc_i\frac{V_{ref}}{V_{outic}}$$

B) measurement of self-inductance $L_{BRi}$

To measure the inductance $L_{BRi}$ of coil $BR_i$, generator 331 controls the application, via controllable voltage source $433_i$, of a sinusoidal AC voltage $Vm_i$ on the terminal of coil $BR_i$ connected to voltage source $433_i$.

Voltage $Vm_i$ may, as in case A), be expressed as follows:

$$Vm_i(t) = V_{ref}\cos(2\pi f_i t)$$

This time, frequency $f_i$ of voltage $Vm_i$ is selected to be close to or greater than the cut-off frequency of the coil (equal to $Rs_{BRi}/2\pi L_{BRi}$), so that the impedance of the inductance of coil $BR_i$ is non-negligible as compared with the series resistance of coil $Rs_{BRi}$. As an example, to measure inductance $L_{BRi}$, frequency $f_i$ is selected to be from 1 to 50 times the cut-off frequency of the coil. As an example, to measure inductance $L_{BRi}$, frequency $f_i$ may be in the range from 1 to 20 kHz for a cut-off frequency in the order of 1 kHz. Preferably, frequency $f_i$ is different from the emission frequency or frequencies of emission device 101. As an example, frequency $f_i$ is smaller than the lowest emission frequency of emission device 101, or greater than the largest emission frequency of emission device 101. Amplitude $V_{ref}$ of voltage $Vm_i$ is selected to avoid saturating operational amplifier $203_i$.

Voltage $Vm_i$ is amplified by transimpedance amplification stage $201_i$. The amplified image of voltage $Vm_i$ thus forms a component of frequency $f_i$ of output voltage $V_{outi}$ of amplification stage $201_i$, expressed as follows:

$$V_{outifi}(t) = V_{ref}\cos(2\pi f_i t)\frac{Rc_i}{Rs_{BRi} + L_{BRi}j\omega}$$

The detection unit of processing device 121 is capable of extracting peak value $V_{outifi}$ of frequency component $f_i$ of signal $V_{outi}$, expressed as follows:

$$V_{outifi} = \frac{V_{ref}}{2} \frac{Rc_i}{\sqrt{Rs_{BRi}^2 + L_{BRi}^2 \omega^2}}$$

Based on this peak value, processing device 121 may determine the value of inductance $L_{BRi}$ by the following formula:

$$L_{BRi} = \frac{1}{\omega}\sqrt{\left(\frac{Rc_i}{2}\frac{V_{ref}}{V_{outifi}}\right)^2 - Rs_{BRi}^2}$$

C) measurement of mutual inductance $Ml_{i,i'}$

To measure the coefficient $Ml_{i,i'}$ of mutual inductance between two receiver coils $BR_i$ and $BR_{i'}$, generator 331 controls the application, via controllable voltage source 433$_i$, of a sinusoidal AC voltage $Vm_i$ on the terminal of coil $BR_i$ connected to voltage source 433$_i$. Voltage $Vm_i$ may, as in cases A) and B), be expressed as follows:

$$Vm_i(t) = V_{ref}\cos(2\pi f_i t)$$

As in case B), frequency $f_i$ of voltage $Vm_i$ is selected to be close to or greater than the cut-off frequency of the coil, $Rs_{BRi}/2\pi L_{BRi}$, so that the impedance of the inductance of coil $BR_i$ is non-negligible as compared with series resistance $Rs_{BRi}$. As an example, to measure the mutual inductance coefficient, frequency $f_i$ is selected to be from 1 to 50 times the cut-off frequency of the coil. As an example, to measure mutual inductance coefficient frequency $f_i$ may be in the range from 1 to 20 kHz for a cut-off frequency of the coil in the order of 1 kHz. Further, as in case B), frequency $f_i$ is preferably different from the emission frequency or frequencies of emission device 101. As an example, frequency $f_i$ is smaller than the lowest emission frequency of emission device 101, or greater than the largest emission frequency of emission device 101. Amplitude $V_{ref}$ of voltage $Vm_i$ is selected to avoid saturating operational amplifier 203$_i$.

The voltage applied, via controllable current source 433$_{i'}$, to the terminal of coil $Bit_{i'}$ connected to voltage source 433$_{i'}$, is for example zero. Anyway, this voltage comprises no component of frequency $f_i$.

Current $i_{BRi}$ crossing coil $BR_i$ is coupled to output voltage $Vout_i$ of transimpedance amplifier 201$_i$ by the following relation:

$$i_{BRi}(t) = \frac{V_{outi}(t)}{Rc_i}$$

Under the effect of this sinusoidal current, coil $BR_i$ emits an AC electromagnetic field of frequency $f_i$. This field is captured by coil $BR_{i'}$, inducing across coil $Bit_{i'}$ a voltage $v_{BRi'}$ expressed as follows:

$$v_{BRi'}(t) = -j\omega Ml_{i,i'} i_{BRi}(t)$$

This voltage is amplified by transimpedance amplification stage 201$_{i'}$, which outputs a voltage $V_{outi'}$ expressed as follows:

$$V_{outi'}(t) = -j\omega Ml_{i,i'} i_{BRi}\cos(2\pi f_i t)\frac{Rc_{i'}}{Rs_{BRi'} + L_{BRi'} j\omega}$$

Processing device 121 is capable, based on the signals measured at the output of amplification stages 201$_i$ to 201$_{i'}$, of determining coefficient $Ml_{i,i'}$, which can be expressed as follows:

$$Ml_{i,i'} = \frac{V_{outi'}}{V_{outi}}\frac{Rc_i}{Rc_{i'}}\frac{|Rs_{BRi} + L_{BRi} j\omega|}{\omega}$$

As an example, the different mutual inductance coefficients of assembly 113 of receiver coils, that is, coefficients $Ml_{1,2}$, $Ml_{1,3}$ and $Ml_{1,3}$ in the example of three receiver coils, may be determined simultaneously by using different excitation frequencies $f_i$. As a variation, the different mutual inductance coefficients may be determined sequentially by using a same excitation frequency $f_i$.

The measurement of parameters $Rs_{BRi}$, $L_{BRi}$ and/or $Ml_{i,i'}$ may be performed during a calibration phase prior to a position tracking phase, and/or during the actual position tracking phase. For example the measurements of parameters $Rs_{BRi}$, $L_{BRi}$ and/or $Ml_{i,i'}$ may be performed continuously in parallel with the measurements of the electromagnetic fields from the emission device, provided for the excitation frequency or frequencies applied by the parameter measurement system on the receiver coils to be different from the emission frequencies of the emission device. Further, parameters $Rs_{BRi}$, $L_{BRi}$ and/or $Ml_{i,i'}$ may be measured simultaneously as soon as the excitation frequencies used to measure them are different from one another.

As an example, generator 331 may comprise a digital frequency synthesizer (not shown) capable of generating one or a plurality of sinusoidal signals having controllable frequencies and, possibly, of adding these signals. The controllable voltage source 433$_i$ associated with each coil for example comprises a digital-to-analog converter (not shown) having its input coupled to a digital output of the frequency synthesizer, and having its output coupled to coil $BR_i$. As a variation, a resistive voltage dividing bridge may be provided between the output of the digital-to-analog converter and the end of coil $BR_i$ connected to voltage source 433$_i$, to adjust the level of the excitation voltage applied to coil $BR_i$.

An advantage of the locating system described in relation with FIGS. 3 and 4 is that it enables to measure possible drifts of certain parameters of the reception device. Knowing such drifts, it is in particular possible to correct the field values measured by the reception device, and thus to improve the locating accuracy of all the receiver coils with respect to know locating systems.

Specific embodiments have been described. Various alterations, modifications, and improvements will readily occur to those skilled in the art.

In particular, the described embodiments are not limited to the above-mentioned application to the locating of surgical tools, but may apply to other fields requiring accurately locating an object in a reference frame.

Further, the described embodiments are not limited to the above-mentioned example of a locating system with three emitter coils and three receiver coils, but more generally apply to any electromagnetic locating system comprising at least one emitter coil and at least one receiver coil. It should be noted that in the case of a system with a single receiver coil, no measurement of the mutual inductance coefficient is necessary.

More generally, it should be noted that although a system enabling to measure possible drifts of parameters $Rs_{BRi}$, $L_{BRi}$ and/or $Ml_{i,i'}$ has been described, it may be chosen, according to the needs of the application, to only monitor a single one of these parameters, for example, parameter $Rs_{BRi}$ which is generally the most critical, or a subset of these parameters.

Further, although an embodiment where the operations carried out by processing device 121 are implemented in the digital domain has been described hereabove, the described embodiments are not limited to this specific case. As a variation, the operations performed by device 121 may be totally or partly implemented in the analog domain. As an example, the operations of synchronous demodulation and of filtering and/or of synchronous detection may be implemented in the analog domain, and the operations of position calculation based on the measured field values may be implemented in the digital domain.

Such alterations, modifications, and improvements are intended to be part of this disclosure, and are intended to be within the spirit and the scope of the present invention. Accordingly, the foregoing description is by way of example only and is not intended to be limiting. The present invention is limited only as defined in the following claims and the equivalents thereto.

What is claimed is:

1. An electromagnetic position tracking system comprising:
    an electromagnetic field emission device comprising at least one emitter coil and, connected to said at least one emitter coil, a first generator of an electric signal for exciting said at least one emitter coil;
    a device for receiving the electromagnetic field emitted by the emission device, comprising at least one receiver coil and, connected to said at least one receiver coil, a circuit for reading an electric signal induced in said at least one receiver coil; and
    a system for measuring at least one parameter of the reception device, comprising, directly connected to said at least one receiver coil by a conductive track or conductive wire, a second generator of an electric signal for exciting said at least one receiver coil wherein the read circuit comprises, associated with each receiver coil, a sense amplification stage comprising an operational amplifier having its inverting input coupled to the output via a feedback resistor and having its non-inverting input coupled to a node of application of a reference potential, a first end of the receiver coil being connected to the inverting input of the operational amplifier.

2. The system of claim 1, wherein said at least one parameter is a parameter from the group comprising the series resistance and the self-inductance of said at least one receiver coil.

3. The system of claim 2, wherein said at least one parameter comprises the series resistance of each receiver coil, and wherein the measurement system is capable, to measure said series resistance, of applying on one end of the receiver coil a DC voltage or a sinusoidal voltage having a frequency at least 20 times lower than the cut-off frequency of the coil.

4. The system of claim 2, wherein said at least one parameter comprises the self-inductance of each receiver coil, and wherein the measurement system is capable, to measure said self-inductance, of applying on one end of the receiver coil a sinusoidal voltage having a frequency greater than the cut-off frequency of the coil.

5. The system of claim 1, wherein the reception device comprises at least two receiver coils, and wherein said at least one parameter is a parameter from the group comprising the series resistance of each receiver coil, the self-inductance of each receiver coil, and the coefficient of mutual inductance between two receiver coils.

6. The system of claim 5, wherein said at least one parameter comprises the coefficient of mutual inductance between two receiver coils, and wherein the measurement system is capable, to measure said coefficient, of applying on one end of one of the two receiver coils a sinusoidal voltage having a frequency greater than the cut-off frequency of the coil.

7. The system of claim 1, wherein the second generator comprises, associated with each receiver coil, a controllable voltage source connected between the second end of the receiver coil and said node of application of a reference potential.

8. The system of claim 1, wherein the second generator comprises a digital frequency synthesizer.

9. The system of claim 1, wherein said at least one emitter coil comprises three emitter coils oriented along different axes, and wherein said at least one receiver coil comprises three receiver coils oriented along different axes.

10. An electromagnetic position tracking system comprising:
    an electromagnetic field emission device comprising at least one emitter coil and, connected to said at least one emitter coil, a first generator of an electric signal for exciting said at least one emitter coil;
    a device for receiving the electromagnetic field emitted by the emission device, comprising at least one receiver coil and, connected to said at least one receiver coil, a circuit for reading an electric signal induced in said at least one receiver coil; and
    a system for measuring at least one parameter of the reception device, comprising, directly connected to said at least one receiver coil by a conductive track or conductive wire, a second generator of an electric signal for exciting said at least one receiver coil,
    wherein said at least one parameter comprises the series resistance of each receiver coil, and wherein the measurement system is capable, to measure said series resistance, of applying on one end of the receiver coil a DC voltage or a sinusoidal voltage having a frequency at least 20 times lower than the cut-off frequency of the coil.

11. An electromagnetic position tracking system comprising:
    an electromagnetic field emission device comprising at least one emitter coil and, connected to said at least one emitter coil, a first generator of an electric signal for exciting said at least one emitter coil;
    a device for receiving the electromagnetic field emitted by the emission device, comprising at least one receiver coil and, connected to said at least one receiver coil, a circuit for reading an electric signal induced in said at least one receiver coil; and
    a system for measuring at least one parameter of the reception device, comprising, directly connected to said at least one receiver coil by a conductive track or conductive wire, a second generator of an electric signal for exciting said at least one receiver coil,
    wherein said at least one parameter comprises the self-inductance of each receiver coil, and wherein the measurement system is capable, to measure said self-inductance, of applying on one end of the receiver coil a sinusoidal voltage having a frequency greater than the cut-off frequency of the coil.

\* \* \* \* \*